United States Patent [19]

Goodhart et al.

[11] Patent Number: 5,074,426

[45] Date of Patent: Dec. 24, 1991

[54] DIVIDABLE CAPSULE

[75] Inventors: Frank W. Goodhart, Mendham; Chaur-Ming Jan, Randolph, both of N.J.

[73] Assignee: Warner-Lambert Company, Morris Plains, N.J.

[21] Appl. No.: 371,485

[22] Filed: Jun. 27, 1989

Related U.S. Application Data

[63] Continuation-in-part of Ser. No. 300,221, Jan. 19, 1989, abandoned, which is a continuation of Ser. No. 930,601, Nov. 13, 1986, abandoned.

[51] Int. Cl.[5] .......... A61K 9/24

[52] U.S. Cl. .......... 220/4.24; 206/528; 206/530; 206/538; 206/821; 220/DIG. 34; 424/451; 424/454; 424/468

[58] Field of Search .......... 220/4 D, 4 E, DIG. 34, 220/4.21–4.25; 206/528, 529, 530, 538, 539, 821; 215/6, 10; 424/451–464, 467, 468, 471

[56] References Cited

U.S. PATENT DOCUMENTS

| | | | |
|---|---|---|---|
| 462,990 | 11/1891 | Oppenheimer | 206/538 |
| 587,327 | 8/1897 | Planten | 220/DIG. 34 |
| 853,497 | 5/1907 | Carnes | 220/4 D |
| 1,510,260 | 9/1924 | Cyrenius | 220/DIG. 34 |
| 1,626,930 | 5/1927 | Grogg | 215/10 |
| 2,326,411 | 8/1943 | Thompson | 220/4 D |
| 2,340,037 | 1/1944 | Zipper | 220/DIG. 34 |
| 2,502,635 | 4/1950 | Swartz | 206/602 |
| 2,679,281 | 5/1954 | Paulucci | 206/821 |
| 2,936,493 | 5/1960 | Scherer | 206/530 |
| 3,228,784 | 1/1966 | Glassman | 424/451 |
| 3,292,810 | 12/1960 | Schechter | 220/4 E |
| 3,653,500 | 4/1972 | Allisbaugh | 206/530 |
| 4,793,493 | 12/1988 | Makiej, Jr. | 206/538 |
| 4,936,461 | 6/1990 | Makiej, Jr. | 424/467 |

FOREIGN PATENT DOCUMENTS

| | | | |
|---|---|---|---|
| 141397 | 5/1985 | European Pat. Off. . | |
| 816342 | 10/1951 | Fed. Rep. of Germany | 215/10 |
| 1480744 | 5/1967 | France | 424/451 |
| 7610038 | 3/1978 | Netherlands | 424/454 |
| 411660 | 9/1934 | United Kingdom | 215/10 |
| 2148841 | 6/1985 | United Kingdom . | |

*Primary Examiner*—Stephen Marcus
*Attorney, Agent, or Firm*—Ronald A. Daignault

[57] ABSTRACT

A capsule which is dividable into accurate individual dosage units by the user is comprised of first and second capsule units, each being cylindrical about a longitudinal axis along the major part of its length. The capsule units are detachably joined in such manner that the longitudinal axes of the two capsule units are approximately co-linear. The capsule units may be detachable joined by adhesive, banding, or locking mechanical means, and the capsule may be comprised of two or more units.

17 Claims, 4 Drawing Sheets

FIG.1
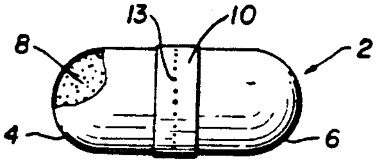
FIG.2
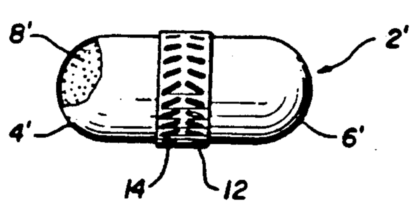
FIG.3
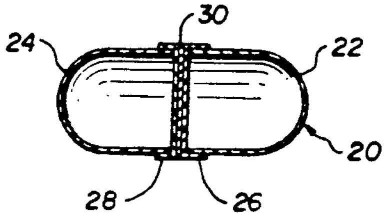
FIG.4
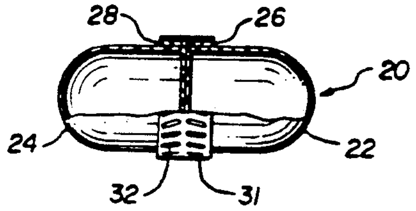
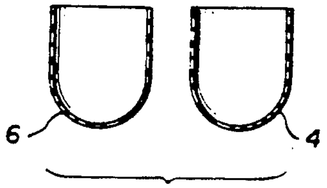
FIG.5
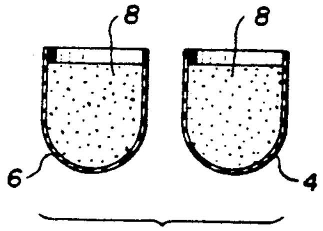
FIG.6
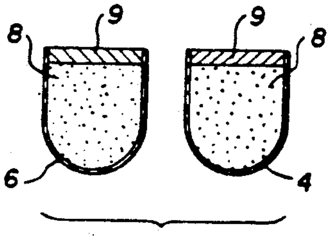
FIG.7
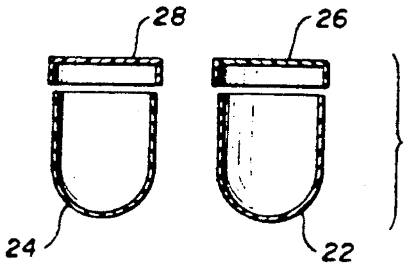
FIG.8

FIG. 17
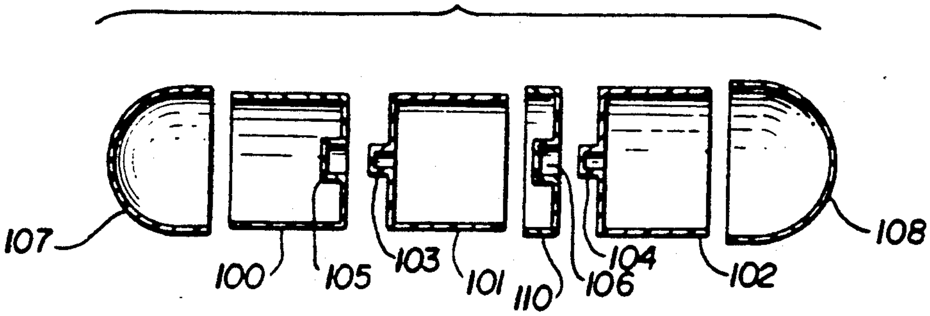
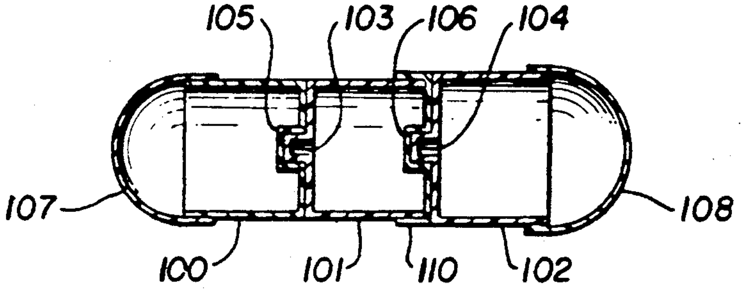
FIG. 18
FIG. 19
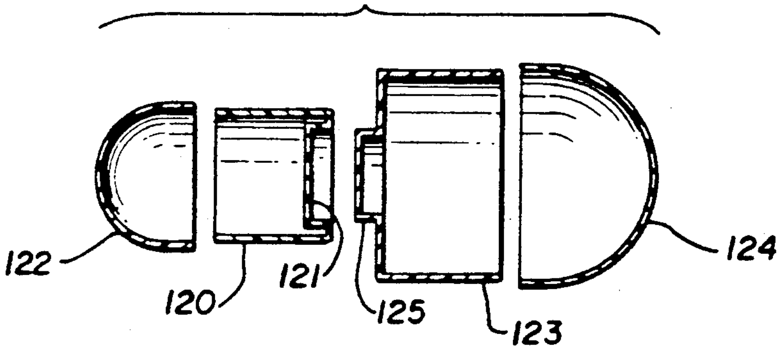
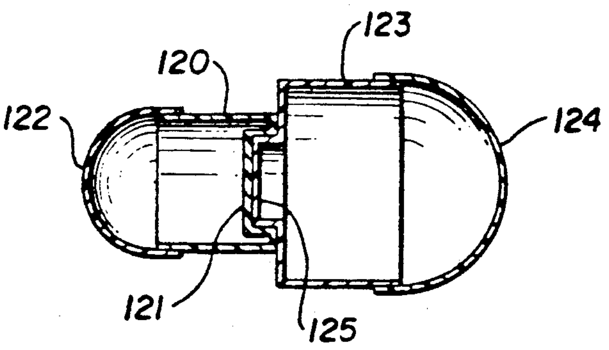
FIG. 20

DIVIDABLE CAPSULE

This application is a continuation-in-part of Ser. No. 07/300,221, filed Jan. 19, 1989, now abandoned, which was a continuation of Ser. No. 06/930,601, filed Nov. 13, 1986, now abandoned.

The present invention is directed to capsules which are dividable by the user into accurate individual dosage units.

It is desirable for a patient to be able to administer medicine to him or herself in varying dosages. Thus, a patient may begin medication in larger dosages, and then proceed to smaller dosages, or vice versa, as treatment progresses. Also, different dosages may be desirable for different individuals. Some drugs require monitoring of drug blood level until the patient is stabilized and dividable dosage forms provide a non-complicated procedure for achieving this.

In the case of tablets, the need for variable dose administration is easily met, since tablets are breakable into smaller units and sometimes may be scored to facilitate breaking into accurate dosage units.

In the case of a capsule however, breaking or division is not ordinarily possible without destroying the integrity of the capsule and losing some or all of the contents.

While providing capsules in varying sizes is possible, it may not be feasible to predict in advance how many capsules in which sizes are necessary for a given patient. In addition, production of capsules in varying sizes complicates the manufacturing process and adds to the patients cost in the event the dosage must be changed.

Additionally, dividable capsules are desirable since they may be used to separate drugs which are interactive, for example, propoxyphene in its hydrochloride or other suitable salt form and aspirin or sodium meclofenamate and codeine sulfate. Further, they may be arranged so as to formulate a portion of the capsule to be slow releasing while the other portion furnishes drug in a readily available fast-dissolving form, or to include two or three sections all having modified release properties which will afford optimal drug blood levels or by attaching a separate section which has enteric properties.

While dividable capsules are known in the prior art, it is believed that the capsules provided by the present invention afford advantages not heretofore realized.

European Patent Publication No. 0 141 397 discloses a dividable capsule which when undivided is in the shape of a conventional capsule. The capsule is dividable along a plane running along the entire length of the capsule and bisecting it by twisting the two "half capsule" parts away from each other. The result is two capsule units, each of which has a cross-section in the shape of a semi-circle and a flat, planar surface which previously had been connected to the flat, planar surface of the other capsule unit.

The disadvantage of this configuration is that the unfamiliar shape of the "half-capsule", which includes a flat surface, may be unpalatable for the patient to swallow. Additionally, due to the unusual shape of each capsule unit, it is not possible to use conventional capsule filling equipment to fill the capsule units with medicine.

United Kingdom Published Patent Appl. No. 2,148,841A discloses dividable capsules which are formed with integrally molded connection elements. For example, a number of capsule bodies would be manufactured with integrally molded webs between and connecting adjacent capsule bodies, while the capsule caps might also have such integrally molded connection elements.

The disadvantage of this arrangement is that conventional capsule bodies and caps cannot be used, and the need for integrally molded interconnection elements considerably complicates manufacture.

It is thus an object of the present invention to provide a dividable capsule which is easily separated by a pull or bending into capsule units which are of familiar and palatable shape.

It is a further object of the present invention to provide a dividable capsule which may utilize conventional capsule bodies or caps.

It is still a further object of the invention to provide a dividable capsule which is relatively easy and straightforward to manufacture and which permits the use of conventional capsule filling equipment.

In accordance with the invention, the above objects are accomplished by providing a dividable capsule which is comprised of first and second capsule units, each of which is cylindrical about an axis along the major part of its length, and wherein the capsule units are detachably joined to each other in such manner that the longitudinal axes of the respective capsule units are approximately co-linear. As used herein, the term "cylindrical" encompasses tubular shapes having circular cross-sections as well as more oval cross-sections such as elliptical cylinders.

While a cylindrical shape is preferred, capsules of other shapes are contemplated. Thus, those having octagonal, hexagonal, square, or other geometrical cross sections are operable. Capsule shapes which resemble tablets (i.e., which are not significantly elongated) can be made.

The capsule units are detachably joined to each other by various expedients including connection by adhesive, an annular band, and locking mechanical means.

The invention will be better appreciated by referring to the accompanying drawings in which:

FIGS. 1-4 are illustrations of a dividable capsule in accordance with several embodiments of the invention.

FIGS. 5-7 illustrate a method of making the dividable capsules of the invention.

FIG. 8 relates to a method of making the embodiment of FIG. 3.

Figure 9:
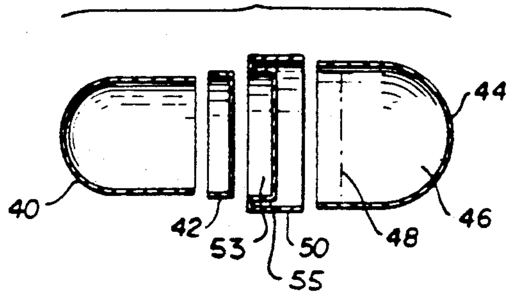

FIG. 9 illustrates the assembly of a dividable capsule in accordance with a further embodiment of the invention.

Figure 10:
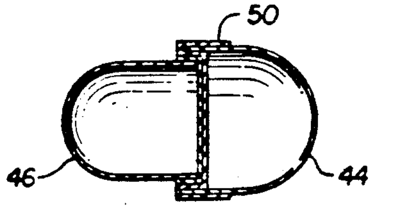

FIG. 10 illustrates the dividable capsule shown in FIG. 9 as assembled.

Figure 11:
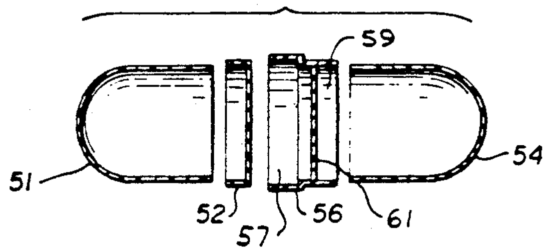

FIG. 11 shows the assembly of a dividable capsule in accordance with still a further embodiment of the invention.

Figure 12:
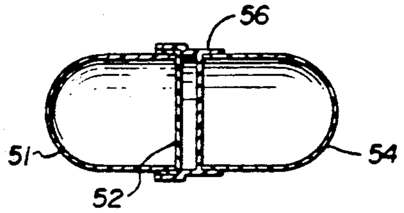

FIG. 12 shows the dividable capsule of FIG. 11 as assembled.

Figure 13:
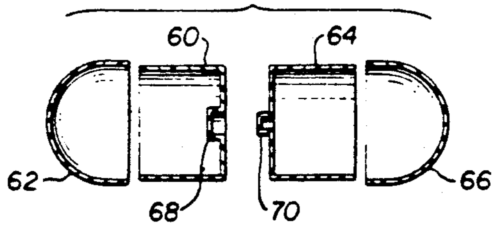

FIG. 13 shows the assembly of a dividable capsule in accordance with still a further embodiment of the invention.

Figure 14:
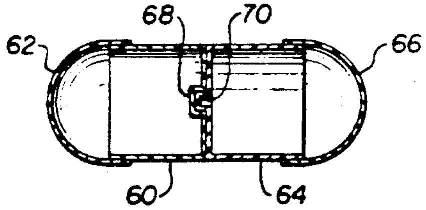

FIG. 14 shows the embodiment of FIG. 13 as assembled.

Figure 15:
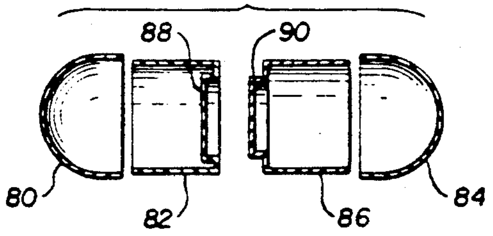

FIG. 15 shows the assembly of a dividable capsule in accordance with still a further embodiment of the invention.

Figure 16:
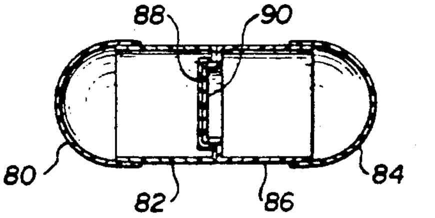

FIG. 16 shows the dividable capsule of FIG. 15 as assembled.

FIG. 17 shows the assembly of a dividable capsule which is comprised of three units.

FIG. 18 shows the dividable capsule of FIG. 17 as assembled.

FIG. 19 shows the assembly of a dividable capsule wherein the units are of different diameters.

FIG. 20 shows the capsule of FIG. 19 as assembled.

Figure 21:
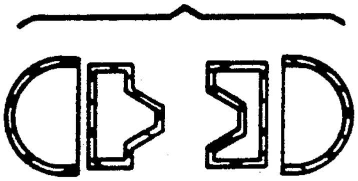
Figure 22:
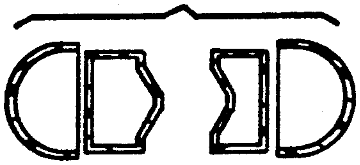
Figure 23:
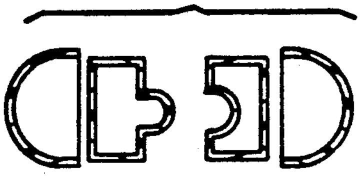

FIGS. 21–23 show the assembly of the body portions of two units with further locking embodiments of the invention.

Figure 24:
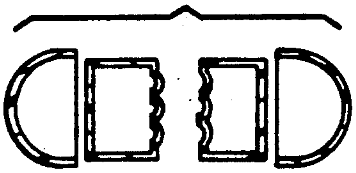

FIG. 24 shows the assembly of the body portions of two units with a further locking embodiment of the invention.

Figure 25:
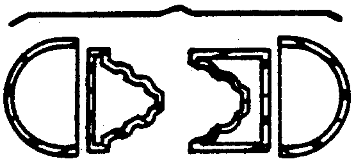
Figure 26:
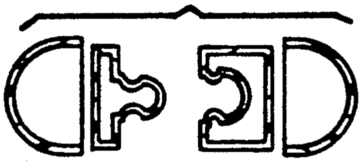

FIGS. 25 and 26 show the assembly of the body portions of two units with still another locking embodiment of the invention.

Referring to FIG. 1, dividable capsule 2 is shown. It is comprised of capsule units 4 and 6, each of which is filled with a desired medicinal preparation 8.

The overall shape of capsule 2 is similar to that of a conventional capsule. That is, each of the capsule units 4 and 6 is comprised of a shell which is cylindrical about an axis over the major portion of its length and rounded at one end.

In addition to the conventional capsule, the one end of the capsule units may also be rectangular or squared if desired.

The capsule units are juxtaposed longitudinally so that the cylindrical axes of the respective capsule units are approximately co-linear and are detachably secured to each other in this configuration.

The capsule units are secured by an adhesive and/or an annular band. In the embodiment of FIG. 1, band 10 is provided which is a thin plastic band of the type sometimes used to secure the bodies and caps of conventional capsules together. The band is perforated at 13 to permit easy separation of the capsule units from each other.

In the embodiment of FIG. 2, the band is an annular sleeve 12 having constrictive segments 14 to provide a friction fit. For example, the constrictive segments may be dimples or other raised areas.

The capsules depicted in FIGS. 1 and 2 may be taken as shown to provide a full dose or may be separated from each other by the user to provide a convenient half dose.

It should be noted that while the capsules shown in the illustrative embodiments are bisectable capsules which provide accurate half doses, if desired, the capsules may be dividable in some other proportion, for example, one-third to two-thirds. Conceivably, the capsule could be a series of segments held together as shown and used for dose titration purposes.

A method of making the dividable capsules is shown in FIGS. 5–7. Referring to FIG. 5, capsule units 4 and 6 are shown. These may be the caps of conventional capsules, typically comprised of a capsule body and capsule cap, and are frequently made of hard gelatin, but may be made of other suitable material. Instead of the capsule caps, capsule bodies may be used, and as these are longer, it may be desirable to cut them, for example, to two-thirds length.

Referring to FIG. 6, the capsule units are filled with a desired medicinal preparation. This, for example, may be in the form of pellets, granules, or viscous or liquid substance. Additionally, the filling step may be performed with the automatic filling machines customarily used to fill conventional capsules.

The capsule units would be filled to within a small distance of the top, for example about one-sixteenth of an inch, and as shown in FIG. 7, a thin layer 9 of adhesive paste would be applied to the top to seal in the medicinal preparation.

The capsule units would then be turned inwardly towards each other with the adhesive paste layers abutting each other, and adhesive paste would be applied to the inside and outside of the joint area, after which the joint would be air dried.

After this, a band or sleeve as shown in FIGS. 1 and 2 would be added.

The adhesive paste used as described above, by way of illustration, could be a polymer solution as follows:

| | |
|---|---|
| HPMC E-15 | 12% w/w |
| PEG 3350 | 2.4% w/w |
| Alcohol, Denatured | 75.4% |
| Water | 10.2% w/w |

Further embodiments of the dividable capsule of the invention are shown in FIGS. 3 and 4. In these embodiments, the capsule units are as shown in FIG. 8, and each comprises a body portion and a cap, wherein the cap has a flat surface and is fitted to snugly fit over the body portion.

The caps are bonded to each other with adhesive paste 30 as shown in FIG. 3 or by a separately molded section which is sealed to the capsule section by means of solvent welding.

In the embodiment shown in FIG. 4, a band 31 having constrictive segments 32 is also added. It is possible that in this embodiment one may dispense with the adhesive paste.

FIGS. 9–16 illustrate further embodiments of the invention wherein locking mechanical means is used to join the two capsule units.

Referring to FIG. 9, capsule units 40 and 44 are shown filled with medicinal preparation 46. Capsule unit 40 is enclosed by cap 42 while capsule unit 44 is closed by adhesive layer 48 or by a friction fit with or without use of a solvent seal.

Intermediate molded locking part 50 is used to secure the two capsule units together. Locking part 50 has open cylindrical receptacle 53 and annular groove 55. Cap 42 of capsule unit 40 is held snugly in annular groove 55. The molded piece may be made of the same material as the capsule units and the dividable capsule as assembled is shown in FIG. 10.

Referring to the embodiment of FIG. 11, capsule unit 51 is closed by cap 52 and intermediate molded piece 56 serves both as a closure for capsule unit 54 and as a connecting means to secure the two capsule units together.

Molded piece 56 has open cylindrical receptacles 57 and 59, which are separated by flat surface 61. Receptacle 57 is sized so as to snugly receive cap 52 of capsule unit 51 while receptacle 59 is sized so as to receive capsule unit 54 in such manner that flat surface 61 acts as a closure for the medicinal preparation in capsule unit 54.

Additionally, the receptacles 57 and 59 may have friction fit features such as dimples to enhance the tightness with which the capsule units are held together. The assembled capsule units are shown in FIG. 12.

A further embodiment to the invention is shown in FIG. 13 wherein cylindrical capsule unit parts 60 and 64 are shown. Each of these capsule unit parts is filled with a desired medicinal preparation, and the capsule unit parts are sealed with rounded or flat caps 62 and 66 respectively. The other end of capsule unit 60 is provided with a female member 68 which may for example be cylindrical receptacle, while capsule unit 64 is provided with a male member 70, which for example may be a cylindrical projection resembling a spike. The male and female members are sized so as to provide a tight friction fit, which may be enhanced by the provision of additional locking means such as one or more dimples on one of the members and a corresponding number of detents on the other of the members. Capsule unit parts 60 and 64 may be made of hard gelatin or other known material used for capsule bodies. The assembled dividable capsule is shown at FIG. 14.

FIGS. 15 and 16 illustrate a dividable capsule which is similar to that shown in FIGS. 13 and 14, except that the locking receptacle and projection are larger in diameter.

FIG. 17 illustrates a dividable capsule which is comprised of three units instead of two. The units are body 100/cap 107, body 102/cap 108, and body 101/cap 110. As shown, cap 110 has a cylindrical receptacle 106 therein, and the units are detachably joined to each other by cylindrical projections 103 and 104, which fit into receptacles 105 and 106. Alternatively, center capsule unit 101/110 could have a receptacle at each end for receiving projections associated with the end capsule units or could have a projection at each end for insertion into receptacles which would be associated with the end units. In FIG. 18, the capsule shown in FIG. 17 is depicted in assembled form.

The embodiment illustrated in FIGS. 19 and 20 is similar to the embodiment of FIGS. 15 and 16, except that one of the capsule units is of greater diameter than the other.

The embodiments shown in FIGS. 21-23 comprise any dividable capsule described above with the body portion of the units to be joined together designed to improve centration. These conical shaped locking means, a male and corresponding female member, seat together to allow tolerance in the machinery of the individual units. Thus even if the machinery of the units cause irregular alignments, the units will still seat together in an easier manner.

The locking embodiment shown in FIG. 24 also shows the body portion of two units to be assembled. This design not only improves centration as described for FIGS. 21-23 but also improves the facility of pulling apart both units when used by the patient.

FIGS. 25 and 26 also show further improvements on the locking means of the body portions of the capsule units in FIGS. 21-23 by adding nubs, slots or rings.

The embodiments shown in FIGS. 13 to 26 may be particularly advantageous in that the dividable capsule can be easily separated by a pulling, bending or twisting motion without the necessity of breaking or tearing a part of the capsule. This relatively easy method of separation is congruent with more practical and trouble-free manufacture.

Thus, there has been described a dividable capsule and illustrative embodiments thereof in accordance with the invention. While the description has been in connection with such illustrative embodiments, it should be appreciated that variations will occur to those skilled in the art and that it is intended that the scope of the invention be limited only by the claims appended hereto and equivalents.

We claim:

1. A capsule which is dividable by the user into accurate individual dosage units for administering a medicine or medicines to the user in varying dosages, comprising first and second capsule units, each for holding a desired medicinal preparation, each of said first and second capsule units being of cylindrical shape at least along most of its length, the cylindrical shaped portion of each capsule unit having a longitudinal axis, and said first and second capsule units having first and second ends, wherein the first ends are rounded and the second end of each said capsule unit is sealed by a closure and wherein said closures of said respective capsule units abut each other and are detachably joined to each other in such manner that the perimeters of each capsule unit abut each other and their respective longitudinal axes are approximately colinear when the units are joined.

2. The dividable capsule of claim 1 wherein said closures are joined together by adhesive.

3. The dividable capsule of claim 1 wherein said closures are joined together by an annular band.

4. The dividable capsule of claim 1 wherein said closures are detachably joined together by locking mechanical means.

5. The dividable capsule of claim 2 where, in addition to said adhesive, said closures are joined together by an annular band.

6. The dividable capsule of claim 2 wherein said closures comprise adhesive layers.

7. The dividable capsule of claim 2 wherein said closures comprise caps.

8. The dividable capsule of claim 3 wherein said closures comprise adhesive layers.

9. The dividable capsule of claim 3 wherein said closures comprise caps.

10. The dividable capsule of claim 3 wherein said annular band has constrictive regions.

11. The dividable capsule of claim 3 wherein said annular band has perforations.

12. The dividable capsule of claim 4 wherein the second end of one of said capsule units is closed by a cap and wherein said locking mechanical means includes a hollow cylindrical member open at one end into which said cap fits.

13. The dividable capsule of claim 12 wherein the second end of the other of said capsule units is closed by an adhesive layer.

14. The dividable capsule of claim 12 wherein the second end of the other of said capsule units is closed by a closure which is a plane member which is integrally formed with said hollow cylindrical member.

15. A capsule which is dividable by the user into accurate individual dosage units for administering a medicine or medicines to the user in varying dosages, comprising first and second capsule units, each for holding a desired medicinal preparation, each of said first and second capsule units being of cylindrical shape at least along most of its length, the cylindrical shaped portion of each capsule unit having a longitudinal axis, and said first and second capsule units having first and second ends, wherein the first ends are rounded and the second end of each said capsule unit is sealed by a closure and wherein said closures of said respective capsule units abut each other and are detachably joined together by locking mechanical means, which comprise interlocking male and female member, and said male member including a conically shaped projection and said female member including a conically shaped receptacle for locking said members together, and wherein the perimeters of each capsule unit abut each other and their respective longitudinal axes are approximately colinear when the units are joined.

16. The dividable capsule of claim 15 having up to three projections and receptacles on the male and female members.

17. The dividable capsule of claim 15 wherein the conically shaped projection and receptacle contain thereon nubs, slots or rings.

* * * * *